United States Patent
Schurter et al.

Patent Number: 5,369,083
Date of Patent: Nov. 29, 1994

[54] SULFONYLUREAS

[75] Inventors: Rolf Schurter, Binningen; Werner Föry, Riehen, both of Switzerland

[73] Assignee: Ciba-Geigy Corporation, Ardsley, N.Y.

[21] Appl. No.: 97,144

[22] Filed: Jul. 26, 1993

[30] Foreign Application Priority Data

Jul. 30, 1992 [DE] Germany ............... 92810582

[51] Int. Cl.$^5$ .................. C07D 239/42; A01N 43/54
[52] U.S. Cl. ..................... 504/215; 544/320
[58] Field of Search ............ 504/215; 544/320

[56] References Cited

U.S. PATENT DOCUMENTS

| | | | |
|---|---|---|---|
| 4,546,179 | 10/1985 | Kunz | 544/206 |
| 4,579,583 | 4/1986 | Föry et al. | 71/92 |
| 5,221,315 | 6/1993 | Föry et al. | 504/178 |

FOREIGN PATENT DOCUMENTS

| | | |
|---|---|---|
| 1243674 | 10/1988 | Canada . |
| 101670 | 2/1984 | European Pat. Off. . |
| 103543 | 3/1984 | European Pat. Off. . |
| 459949 | 12/1991 | European Pat. Off. . |
| 662348 | 9/1987 | Switzerland . |

OTHER PUBLICATIONS

Derw. Abst. 85-154598/26 of CH 662348 (1985).

*Primary Examiner*—John M. Ford
*Attorney, Agent, or Firm*—Marla J. Mathias; George R. Dohmann

[57] ABSTRACT

N-Pyridylsulfonyl-N'-pyrimidinylureas of formula I

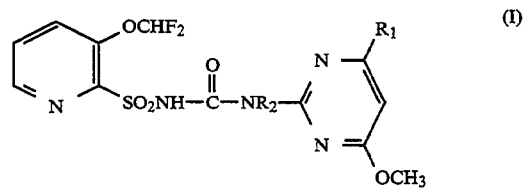

wherein $R_1$ is methyl or methoxy and $R_2$ is hydrogen or methyl;

and the salts of those compounds with mines, alkali metal or alkaline earth metal bases or with quaternary ammonium bases, have good pre- and post-emergence selective herbicidal and growth-regulating properties.

9 Claims, No Drawings

SULFONYLUREAS

The present invention relates to novel herbicidally active N-pyridylsulfonyl-N'-pyrimidinylureas, to processes for the preparation thereof, to compositions comprising them as active ingredients, and to the use thereof in the control of weeds, especially selectively in crops of useful plants, or for regulating and inhibiting plant growth.

Phenylsulfonylureas having herbicidal activity are known from European Patent Application No. 0 103 543. The compounds specifically disclosed therein are not always capable, however, of fulfilling requirements in terms of strength of action and spectrum of activity. There is therefore a need for more effective and more selective compounds.

Novel sulfonylureas having improved herbicidal properties have now been found.

The novel sulfonylureas have the formula I

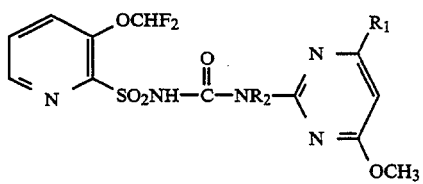

wherein
$R_1$ is methyl or methoxy and
$R_2$ is hydrogen or methyl;
and the salts of those compounds with amines, alkali metal or alkaline earth metal bases or with quaternary ammonium bases.

The invention relates also to the salts that the compounds of formula I are capable of forming with amines, alkali metal and alkaline earth metal bases or with quaternary ammonium bases.

Alkali metal and alkaline earth metal hydroxides that are especially suitable as salt formers are the hydroxides of lithium, sodium, potassium, magnesium and calcium, especially those of sodium and potassium.

Examples of amines suitable for the formation of ammonium cations are both ammonia and primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four isomeric butylamines, n-amylamine, isoamylamine, hexylamine, heptylamine, octylamine, nonylamine, decylamine, pentadecylamine, hexadecylamine, heptadecylamine, octadecylamine, methylethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, such as pyridine, quinoline, isoquinoline, morpholine, piperidine, pyrrolidine, indoline, quinuclidine and azepine; primary arylamines, such as anilines, methoxyanilines, ethoxyanilines, o,m,p-toluidines, phenylenediamines, benzidines, naphthylamines and o,m,p-chloroanilines; but especially triethylamine, isopropylamine and diisopropylamine.

In the compounds of formula I, $R_2$ is preferably hydrogen. A preferred individual compound from the scope of formula I that may be mentioned is: N-(3-difluoromethoxypyridin-2-yl-sulfonyl)-N'-(4-methyl-6-methoxypyrimidin-2-yl)-urea.

The compounds of formula I can be prepared by
a) reacting a pyridylsulfonamide of formula II

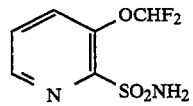

with an N-pyrimidinylcarbamate of formula III

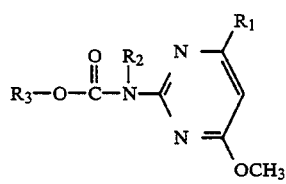

wherein $R_1$ and $R_2$ are as defined for formula I and $R_3$ is phenyl or 4-tolyl, in the presence of a base, or
b) reacting a compound of formula IV

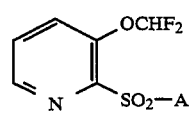

wherein A is

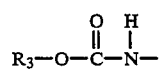

or O=C=N—, wherein $R_3$ is as defined above, in the presence of a base, with a 2-aminopyrimidine of formula V

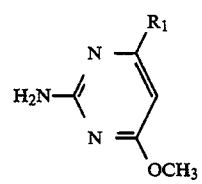

wherein $R_1$ is as defined for formula I, or
c) reacting a pyridylsulfonamide of formula II

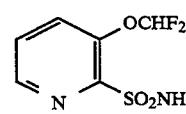

in the presence of a base, with a pyrimidinyl isocyanate of formula VI

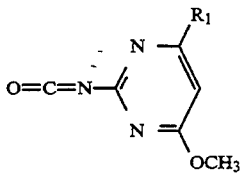

(VI)

wherein R₁ is as defined for formula I, or d) reacting a compound of formula VII

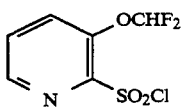

(VII)

with a compound of formula V

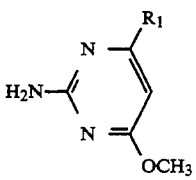

(V)

wherein R₁ is as defined for formula I, in the presence of an ammonium, phosphonium, sulfonium or alkali metal cyanate salt of formula VIII

M⁺OCN⁻ (VIII)

wherein M is an alkali metal or the group $R_4R_5R_6R_7Q$, wherein $R_4$, $R_5$, $R_6$ and $R_7$ independently of one another are $C_1$–$C_{18}$alkyl, benzyl or phenyl, the total number of carbon atoms not exceeding 36; and Q is nitrogen, sulfur or phosphorus.

The reactions to form compounds of formula I are advantageously carried out in aprotic, inert organic solvents. Such solvents are hydrocarbons, such as benzene, toluene, xylene or cyclohexane, chlorinated hydrocarbons, such as dichloromethane, trichloromethane, tetrachloromethane or chlorobenzene, ethers, such as diethyl ether, ethylene glycol dimethyl ether, diethylene glycol dimethyl ether, tetrahydrofuran or dioxane, nitriles, such as acetonitrile or propionitrile, amides, such as dimethylformamide, diethylformamide or N-methylpyrrolidinone. The reaction temperatures are preferably from −20° to +120° C.

The reactions are generally slightly exothermic and can be carried out at room temperature. In order to reduce the reaction time or to initiate the reaction, the reaction mixture is advantageously heated to boiling point for a short time. The reaction times can likewise be reduced by the addition of a few drops of a base as catalyst. Suitable bases are especially tertiary amines, such as trimethylamine, triethylamine, quinuclidine, 1,4-diazabicyclo(2.2.2)octane, 1,5-diazabicyclo(4.3.0)-non-5-ene or 1,5-diazabicyclo(5.4.0)undec7-ene. There may, however, also be used as bases inorganic bases, such as hydrides such as sodium or calcium hydride, hydroxides such as sodium and potassium hydroxide, carbonates such as sodium and potassium carbonate or hydrogen carbonates such as potassium and sodium hydrogen carbonate.

The end products of formula I can be isolated by concentration and/or by evaporation of the solvent and purified by recrystallisation or trituration of the solid residue in solvents in which they are not readily soluble, such as ethers, aromatic hydrocarbons or chlorinated hydrocarbons.

The compounds of formulae II, III, IV, V, VI, VII and VIII are either known or can be prepared analogously to known processes. Process variant a) is described, for example, in EP-A-0 103 543 and process variant b) is described, for example, in EP-A-0 101 670. Process variants c) and d) are disclosed in EP-A-0 459 949 and Swiss Patent No. 662 348.

Various methods and techniques are suitable for the use according to the invention of the compounds of formula I or compositions comprising them. The following are examples thereof:

i) Seed Dressing a) Dressing the seeds with a wettable powder formulation of a compound by shaking in a vessel until the formulation is evenly distributed over the surface of the seeds (dry dressing). Up to 4 g of a compound of formula I (in the case of a 50% formulation: up to 8.0 g of wettable powder) are used per 1 kg of seed.

b) Dressing the seeds with an emulsifiable concentrate of the compound or with an aqueous solution of a wettable powder formulation of the compound of formula I according to method a) (wet dressing).

c) Dressing by immersing the seeds in a mixture comprising up to 1000 ppm of a compound of formula I for 1 to 72 hours and, if desired, subsequently drying the seeds (seed soaking).

Dressing the seed or treating the germinated seedling are naturally the preferred methods of application since the active ingredient treatment is directed wholly at the target crop. Normally 0.001 g to 4.0 g of active ingredient are used per 1 kg of seed, although, depending on the method employed, which also allows the addition of other active ingredients or micronutrients, amounts that exceed or fall short of the specified concentration limits may be employed (repeat dressing).

ii) Controlled Release of Active Ingredient

A solution of the compound is applied to mineral granule carriers or polymerised granules (urea/formaldehyde) and allowed to dry. If desired, a coating may be applied (coated granules) that allows the active ingredient to be released in metered amounts over a specific period of time.

The compounds of formula I can be used in unmodified form, i.e. as obtained from synthesis, but they are preferably formulated in customary manner together with the adjuvants conventionally employed in formulation technology, e.g. into directly sprayable or dilutable solutions, dilute emulsions, wettable powders, soluble powders, dusts, granules or microcapsules. As with the nature of the compositions, the methods of application, such as spraying, atomising, dusting, wetting, scattering or pouting, are chosen in accordance with the intended objectives and the prevailing circumstances.

The formulations, i.e. the compositions, preparations or mixtures comprising the compound (active ingredient) of formula I or at least one compound of formula I and, where appropriate, one or more solid or liquid adjuvants, are prepared in known manner, e.g. by homogeneously mixing and/or grinding the active ingredients with the adjuvants, e.g. solvents or solid carriers. It is also possible for surface-active compounds (surfactants) to be used in the preparation of the formulations.

Suitable solvents are: aromatic hydrocarbons, preferably the fractions containing 8 to 12 carbon atoms, such as mixtures of alkylbenzenes, e.g. xylene mixtures or alkylated naphthalenes; aliphatic and cycloaliphatic hydrocarbons, such as paraffins, cyclohexane or tetrahydronaphthalene; alcohols, such as ethanol, propanol or butanol; glycols and their ethers and esters, such as propylene glycol or dipropylene glycol ether; ketones, such as cyclohexanone, isophorone or diacetone alcohol; strongly polar solvents, such as N-methyl-2-pyrrolidone, dimethyl sulfoxide or water; vegetable oils and esters thereof, such as rape oil, castor oil or soybean oil; and, where appropriate, also silicone oils.

The solid carriers used, e.g. for dusts and dispersible powders, are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending upon the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty alcohol sulfonates, fatty alcohol sulfates, sulfonated benzimidazole derivatives or alkylaryl sulfonates.

The fatty alcohol sulfonates or sulfates are usually in the form of alkali metal salts, alkaline earth metal salts or unsubstituted or substituted ammonium salts and contain a $C_8$–$C_{22}$alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide, or phospholipids.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol polyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic suffactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in formulation technology that may also be used in the compositions according to the invention are described inter alia in the following publications:

"Mc Cutcheon's Detergents and Emulsifiers Annual", Mc Publishing Corp., Glen Rock, N.J. 1988.

M. and J. Ash, "Encyclopedia of Surfactants", Vol. I–III, Chemical Publishing Co., New York, 1980–1981.

Dr. Helmut Stache "Tensid-Taschenbuch" (Surfactant Handbook), Carl Hanser Verlag, Munich/Vienna 1981.

The herbicidal compositions usually comprise 0.1 to 99%, preferably 0.1 to 95%, of a compound of formula I, 1 to 99% of a solid or liquid adjuvant, and 0 to 25%, preferably 0.1 to 25%, of a surfactant.

Whereas commercial products will preferably be formulated as concentrates, the end user will normally employ dilute formulations.

The compositions may also comprise further auxiliaries, such as stabilisers, e.g. vegetable oils or epoxidised vegetable oils (epoxidised coconut oil, rape oil or soybean oil), anti-foams, e.g. silicone oil, preservatives, viscosity regulators, binders and tackifiers, as well as fertilisers or other active ingredients for obtaining special effects.

Preferred formulations have especially the following composition (throughout, percentages are by weight)

Dusts:
| | |
|---|---|
| active ingredient: | 0.1 to 50%, preferably 0.1 to 5% |
| solid carrier: | 99.9 to 90%, preferably 99.9 to 99% |

Suspension concentrates:
| | |
|---|---|
| active ingredient: | 5 to 75%, preferably 10 to 50% |
| water: | 94 to 24%, preferably 88 to 30% |
| surface-active agent: | 1 to 40%, preferably 2 to 30% |

Wettable powders:
| | |
|---|---|
| active ingredient: | 0.5 to 90%, preferably 1 to 80% |
| surface-active agent: | 0.5 to 20%, preferably 1 to 15% |

| | |
|---|---|
| solid carrier: | 5 to 95%, preferably 15 to 90% |
| Grannules: | |
| active ingredient: | 0.1 to 30%, preferably 0.1 to 15% |
| solid carrier: | 99.5 to 70%, preferably 97 to 85% |

The compounds of formula I are generally used successfully at rates of application of from 0.001 to 2 kg/ha, especially from 0.005 to 1 kg/ha. The concentration required to achieve the desired effect can be determined by experiment. It is dependent upon the type of action, the stage of development of the crop plant and of the weed, and also upon the application (place, time, method) and, in dependence on those parameters, can vary within wide limits.

The compounds of formula I are distinguished by growth-inhibiting and herbicidal properties that make them outstandingly suitable for use in crops of useful plants, especially in cereals, cotton, soybeans, rape, sugar cane, plantation crops, maize and rice, the use thereof in maize crops being very especially preferred.

The preparation of the compounds of formula I is explained in greater detail in the following Examples.

EXAMPLE P1: Preparation of 2-isopropylthio-3-hydroxypyridine:

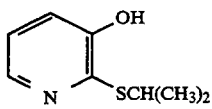

At a temperature of +5° C., 14 g of potassium tert-butoxide are added in portions to a solution of 16.4 g of 2-mercapto-3-hydroxypyridine (known from Tetrahedron 21, 2191, (1980)) in 155 ml of dimethylformamide. Then, at a temperature of from 0° to +2° C., 12.5 ml of isopropyl iodide are added dropwise thereto in the course of 15 minutes. After stirring for 2 hours at room temperature, the reaction mixture is extracted with 400 ml of ice water and 200 ml of ethyl acetate. The pH value is adjusted to from 7 to 8 with 2N hydrochloric acid and then the aqueous phase is washed four times with 150 ml of ethyl acetate each time. The combined organic phases are washed three times with 100 ml of water each time, concentrated in vacuo to a volume of 100 ml and, at a temperature of 0° C., extracted four times with 50 ml of 2N aqueous sodium hydroxide solution each time. The aqueous phase is then adjusted to a pH value of from 7 to 8 with 2N hydrochloric acid and extracted four times with 50 ml of ethyl acetate each time. Drying of the organic phase, filtering over 100 g of silica gel, washing four times with 50 ml of ethyl acetate each time and concentrating by evaporation yield a crystallising residue which is triturated with petroleum ether and then filtered to yield 14.6 g of 2-isopropylthio-3-hydroxypyridine having a melting point of 64° C.

EXAMPLE P2: Preparation of 2-isopropylthio-3-difluoromethoxypyridine:

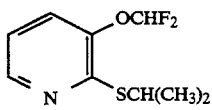

In the course of 15 minutes, 464 ml of 30% aqueous sodium hydroxide solution are added dropwise to a solution of 118.4 g of 2-isopropylthio-3-hydroxypyridine in 560 ml of dioxane. Then in the course of 2 hours, at a temperature of 80° C., 121 g of Freon-22 are introduced and the reaction mixture is stirred for a further 90 minutes. The reaction mixture is cooled to room temperature and then extracted with a mixture of 2500 ml of ice water and 1000 ml of methylene chloride and the phases are washed four times with 50 ml of methylene chloride each time and once with 100 ml of ice water. The combined organic phases are then dried over sodium sulfate and concentrated by evaporation in vacuo. Purification by silica gel chromatography with ethyl acetate/n-hexane 1:9 as eluant yields 105.7 g of 2-isopropylthio-3-difluoromethoxypyridine in the form of an oil having an $n_D^{21}$ of 1.5088.

EXAMPLE P3: Preparation of 3-difluoromethoxypyridin-2-yl-sulfonamide:

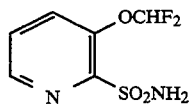

In the course of 50 minutes, at a temperature of from −5° to 0° C., 142 g of gaseous chlorine are introduced into a mixture of 105.7 g of 2-isopropylthio-3-difluoromethoxypyridine, 1000 ml of dichloromethane and 1723 ml of 1N hydrochloric acid. After stirring for 20 minutes at a temperature of −30° C., nitrogen is introduced in the course of 15 minutes. The phases are then washed three times with 250 ml of ice water and 250 ml of dichloromethane each time and the combined organic phases are dried over sodium sulfate. The reaction mixture is then added dropwise in the course of 40 minutes, at a temperature of from −50° to −40° C., to a mixture of 122.7 g of ammonia in 250 ml of dichloromethane. After being stirred for 15 hours and then filtered, the reaction mixture is concentrated by evaporation and triturated with petroleum ether, and the resulting crystal agglomerate is filtered and dried to yield 85.9 g of 3-difluoromethoxypyridin-2-yl-sulfonamide having a melting point of from 85° to 86° C.

EXAMPLE P4: Preparation of N-(3-difluoromethoxypyridin-2-yl-sulfonyl)-N'-(4-methyl-6-methoxypyrimidin-2-yl)-urea (Compound No. 1.03):

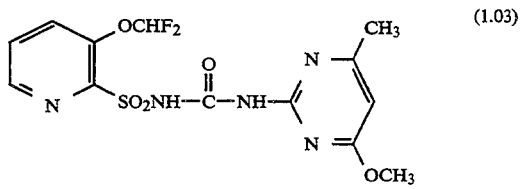

(1.03)

4.97 g of N-(4-methyl-6-methoxypyrimidin-2-yl)-phenylcarbamate and 2.95 ml of 1,5-diazabicyclo[5.4.-0]undec-5-ene are added in succession to a solution of 4.03 g of 3-difluoromethoxypyridin-2-yl-sulfonamide in 40 ml of acetonitrile. The reaction mixture is stirred for 60 minutes and then concentrated in vacuo. The oily residue thus obtained is then triturated with 12 ml of 2N hydrochloric acid and diluted with 10 ml of water. The crystallised product is filtered and then washed in succession with water and diethyl ether to yield N-(3-diifluoromethoxypyridin-2-yl-sulfonyl)-N'-(4-methyl-6-methoxypyrimidin-2-yl)-urea (Compound 1.03) having a melting point of from 151° to 154° C.

The compounds of formula I listed in the following Table 1 and their intermediates are prepared in analogous manner.

TABLE 1

Compounds of formula I:

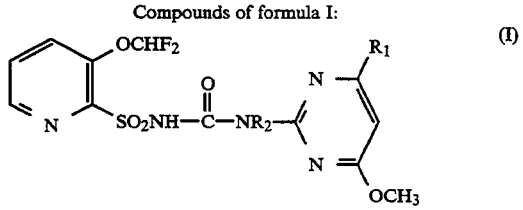

| Comp. No. | R₁ | R₂ | phys. data |
|---|---|---|---|
| 1.01 | OCH₃ | H | m.p. 137–139° C. |
| 1.02 | OCH₃ | CH₃ | |
| 1.03 | CH₃ | H | m.p. 151–154° C. |
| 1.04 | CH₃ | CH₃ | |

Formulation Examples for Active Ingredients of Formula I (throughout, percentages are by weight)

| F1. Wettable powders | a) | b) | c) | d) |
|---|---|---|---|---|
| a compound of Table 1 | 1% | 5% | 25% | 50% |
| sodium lignosulfonate | 3% | 4% | — | 3% |
| sodium larylsulfate | — | — | 3% | 1% |
| sodium diisobutylnaphthalene solfonate | — | 3% | 6% | 5% |
| octylphenyl polyglycol ether (7–8 mole of ethylene oxide) | 2% | 1% | — | — |
| highly dispersed silicic acid | 2% | 2% | 5% | 5% |
| kaolin | 42% | 35% | 61% | 36% |
| sodium chloride | 50% | 50% | — | — |

The active ingredient is thoroughly mixed with the adjuvants and the mixture is thoroughly ground in a suitable mill, affording wettable powders which can be diluted with water to give suspensions of the desired concentration.

| F2. Coated granules | a) | b) | c) |
|---|---|---|---|
| a compound of Table 1 | 0.1% | 5% | 15% |
| highly dispersed silicic acid | 0.9% | 2% | 2% |
| inorganic carrier (diameter 0.1–1 mm) such as CaCO₃ or SiO₂ | 99.0% | 93% | 83% |

The active ingredient is dissolved in methylene chloride and sprayed onto the carrier, and the solvent is then evaporated off in vacuo.

| F3. Coated granules | a) | b) | c) |
|---|---|---|---|
| a compound of Table 1 | 0.1% | 5% | 15% |
| polyethylene glycol (mol. wt. 200) | 1.0% | 2% | 3% |
| highly dispersed silicic acid | 0.9% | 1% | 2% |
| inorganic carrier (diameter 0.1–1 mm) such as CaCO₃ SiO₂ | 98.0% | 92% | 80% |

The finely ground active ingredient is uniformly applied, in a mixer, to the carrier moistened with the polyethylene glycol. Non-dusty coated granules are obtained in this manner.

| F4. Extruder granules | a) | b) | c) | d) |
|---|---|---|---|---|
| a compound of Table 1 | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants, and the mixture is moistened with water. The mixture is extruded and then dried in a stream of air.

| F5. Dusts | a) | b) | c) |
|---|---|---|---|
| a compound of Table 1 | 0.1% | 1% | 5% |
| talcum | 39.9% | 49% | 35% |
| kaolin | 60.0% | 50% | 60% |

Ready-for-use dusts are obtained by mixing the active ingredient with the carriers and grinding the mixture in a suitable mill.

| F6. Suspension concentrates | a) | b) | c) | d) |
|---|---|---|---|---|
| a compound of Table 1 | 3% | 10% | 25% | 50% |
| ethylene glycol | 5% | 5% | 5% | 5% |
| nonylphenol polyclycol ether (15 mol of ethylene oxide) | — | 1% | 2% | 1% |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 37% |

The finely ground active ingredient is intimately mixed with the adjuvants, giving a suspension concentrate from which suspensions of any desired concentration can be obtained by dilution with water.

BIOLOGICAL EXAMPLES

Example B1: Pre-emergence Herbicidal Action

Plastics pots are filled with expanded vermiculite (density: 0.135 g/cm³, water-adsorption capacity: 0.565 l/l). After the non-adsorptive vermiculite has been saturated with an aqueous emulsion in deionised water comprising the active ingredients in a concentration of 70 ppm, seeds of the following plants are sown on the surface: Nasturtium officinalis, Agrostis tenuis, Stellaria media and Digitaria sanguinalis. The pots are then kept in a climatic chamber at a temperature of 20° C., an illumination of approx. 20 klux and 70% relative humidity. During the germination phase of 4 to 5 days, the pots are covered with light-permeable material and watered with deionised water in order to increase the local humidity. After the 5th day, 0.5% of a commercial liquid fertiliser is added to the water. The test is evaluated 12 days after sowing and the action on the test plants is assessed in accordance with the following scale:

1: plant has not germinated or has withered
2–3: very pronounced action
4–6: medium action
7–8: weak action
9: no action (as untreated control)

TABLE B1

Preemergence action:
Concentration of active ingredient emulsion: 70 ppm

Test plant:

| Compound No. | Nasturtium | Stellaria | Agrostis | Digitaria |
|---|---|---|---|---|
| 1.03 | 4 | 3 | 2 | 2 |

Example B2: Post-emergence Herbicidal Action (contact herbicide)

A number of weeds, both monocotyledonous and dicotyledonous, are sprayed post-emergence (in the 4- to 6-leaf stage) with an aqueous active ingredient dispersion according to Example F6 at a rate of 8–500 g of active ingredient per hectare and the plants are kept at 24°–26° C. and 45–60% relative humidity. 15 days after the treatment the test is evaluated.

The herbicidal action is evaluated after 3 weeks in accordance with a scale of nine ratings (1=total damage, 9=no action) in comparison with an untreated control group. Ratings of from 1 to 4 (especially from 1 to 3) indicate good to very good herbicidal action. Ratings of from 6 to 9 (especially from 7 to 9) indicate good tolerance (especially in the case of crop plants).

In this test the compounds of formula I exhibit a pronounced herbicidal action. The same results are obtained when the compounds of formula I are formulated in accordance with Examples F1 to F5.

What is claimed is:

1. An N-pyridylsulfonyl-N'-pyrimidinylurea of formula I

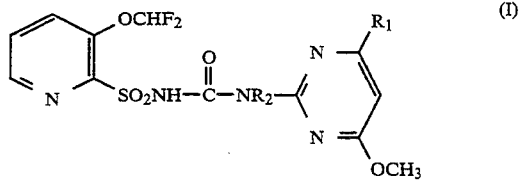

wherein
$R_1$ is methyl or methoxy, and
$R_2$ is hydrogen or methyl, or a salt of such a compound with an amine, an alkali metal or alkaline earth metal base or with a quaternary ammonium base.

2. A compound according to claim 1 wherein $R_2$ is hydrogen.

3. N-(3-Difluoromethoxypyridin-2-yl-sulfonyl)-N'-(4-methyl-6-methoxypyrimidin-2-yl)-urea according to claim 1.

4. A herbicidal and plant-growth-inhibiting composition comprising one or more sulfonyl-ureas of formula I, according to claim 1, and an agrochemically acceptable carrier.

5. A composition according to claim 4 comprising from 0.1% to 95% of a compound of formula I.

6. A method of controlling undesirable plant growth, which comprises applying an effective amount of a compound of formula I, according to claim 1, or of a composition comprising that compound, to the plants or to the locus thereof.

7. A method according to claim 6, which comprises applying active ingredient in an amount of from 0.001 to 2 kg per hectare.

8. A method of inhibiting plant growth, which comprises applying an effective amount of a compound of formula I, according to claim 1, or of a composition comprising that compound, to the plants or to the locus thereof.

9. A method according to claim 7 for the selective pre- or post-emergence control of weeds in crops of useful plants.

* * * * *